US008673880B2

(12) United States Patent
Turnbull et al.

(10) Patent No.: US 8,673,880 B2
(45) Date of Patent: Mar. 18, 2014

(54) PREVENTION AND/OR TREATMENT OF NEURODEGENERATIVE DISORDERS

(75) Inventors: Jeremy Turnbull, Merseyside (GB); Edwin Yates, Merseyside (GB); Susannah Patey, Merseyside (GB)

(73) Assignee: The University Of Liverpool (GB)

( * ) Notice: Subject to any disclaimer, the term of this patent is extended or adjusted under 35 U.S.C. 154(b) by 817 days.

(21) Appl. No.: 12/227,630

(22) PCT Filed: May 23, 2007

(86) PCT No.: PCT/GB2007/001895
§ 371 (c)(1),
(2), (4) Date: Nov. 24, 2008

(87) PCT Pub. No.: WO2007/138263
PCT Pub. Date: Dec. 6, 2007

(65) Prior Publication Data
US 2010/0062998 A1 Mar. 11, 2010

(30) Foreign Application Priority Data
May 25, 2006 (GB) .................................. 0610350.1

(51) Int. Cl.
*A61K 31/727* (2006.01)
(52) U.S. Cl.
USPC ........................................................ 514/56
(58) Field of Classification Search
None
See application file for complete search history.

(56) References Cited

U.S. PATENT DOCUMENTS 5,262,403 A * 11/1993 Nicolson et al. ............. 514/56
5,380,716 A * 1/1995 Conrad et al. .................. 514/56

FOREIGN PATENT DOCUMENTS

| EP | 0354 595 A1 | 2/1990 |
| JP | 03-130230 | 6/1991 |
| WO | 96/23003 A1 | 8/1996 |
| WO | 97/01568 A | 1/1997 |

OTHER PUBLICATIONS

Ross et al. Neurodegeneration, Jul. 2004, pp. S10-S17.*
Definition of neurodegenerative disorder, downloaded from the internet on Mar. 12, 2012.*
PubMed Health—Alzheimer's disease, Nov. 17, 2010.*
Naggi et al. The Journal of Biological Chemistry, vol. 280, No. 13, Apr. 1, 2005, pp. 12103-12113.*
Reduction of azides, Organic Chemistry Portal, http://www.organic-chemistry.org/synthesis/N1H/reductionsazides.shtm, downloaded from the internet Jun. 12, 2013.*
Patey, S.J. et al.; Heparin Derivatives as Inhibitors of BACE-1, the Alzheimer's beta-Secretase, with Reduced Activity Against Factor Xa and Other Proteases, J. Med. Chem., Oct. 5, 2006, 49:20, pp. 6129-6132.
Ferrer I. et al.; Distribution of Fibroblast Growth Factor Receptor-1 (FGFR-1) and FGFR-3 in the Hippocampus of Patients with Alzheimer's Disease, Neurosci. Letters, Ireland, Jan. 16, 1998, 240:3, pp. 139-142.
Wessel, H.P. et al.; Synthesis of an *N-acetylated* Heparin Pentasaccharide and its Anticoagulant Activity in Comparison with the Heparin Pentasaccharide with High Anti-Factor-xa Activity, Helvetica Chimica Acta, 1989, Switzerland, 72:6, pp. 1268-1277.
International Search Report, PCT/GB2007/001895, dated Sep. 19, 2007.
Yates, EA et al., J. Med. Chem 2004, 47, 277-280.
Bergamaschini, L. et al., The Journal of Neuroscience, Apr. 2004, 24(17): 4181-4186.
van Horssen, J. et al., The Lancet Neurology vol. 2 Aug 2003; 2: 482-92.
Scholefield Z et al., J. Cell Biology 2003, 163, 97-107.
Kreuger, J., P. Jemth et al., J. Biochem 2005, 389 (pt, 1), 145-150.
Yates, EA et al., Carbohydrate Research 1996, 294, 15-27.
Jaseja, M et al., Can.J.Chem 1989, 67, 1449-1456.
Santini, F. et al., Carbohydrate Research 1997, 302, 103-108.
Inoue, S. & Miyawaki, M., Analytical Biochemistry 1975, 65, 164-174.
Inoue, Y, and Nagasawa, K., Carbohydrate Research 1976 46, 87-95.
Lloyd, A.G. et al., J.Biochemical Pharmacology 1971, 20, 637-648.
Yates, EA et al., Carbohydrate Research 2000, 329, 239-247.
Yates, EA et al., Carbohydrate Research 1997, 298, 335-340.
Watson, D.J., Lander, A.D. and Selkoe, D.J. 1997. J Biol Chem. 272, 31617-24.

* cited by examiner

*Primary Examiner* — Layla Bland
(74) *Attorney, Agent, or Firm* — Lerner, David, Littenberg, Krumholz & Mentlik, LLP

(57) ABSTRACT

A pharmaceutical composition for use in the prevention and/or treatment of a neurodegenerative disorder comprising a compound comprised of one or more disaccharide units, the or each disaccharide unit comprising a uronate moiety linked to a glucosamine moiety, wherein the 2-O atom of the uronate moiety is substituted with a hydrogen atom, the 6-O atom of the glucosamine moiety is substituted with a sulphate group and the 2-N atom of the glucosamine moiety is substituted with an atom or group other than a sulphate group. The composition is particularly preferred for use in the prevention and/or treatment of Alzheimer's disease.

10 Claims, 2 Drawing Sheets

PREVENTION AND/OR TREATMENT OF NEURODEGENERATIVE DISORDERS

CROSS REFERENCE TO RELATED APPLICATIONS

Figure 1:
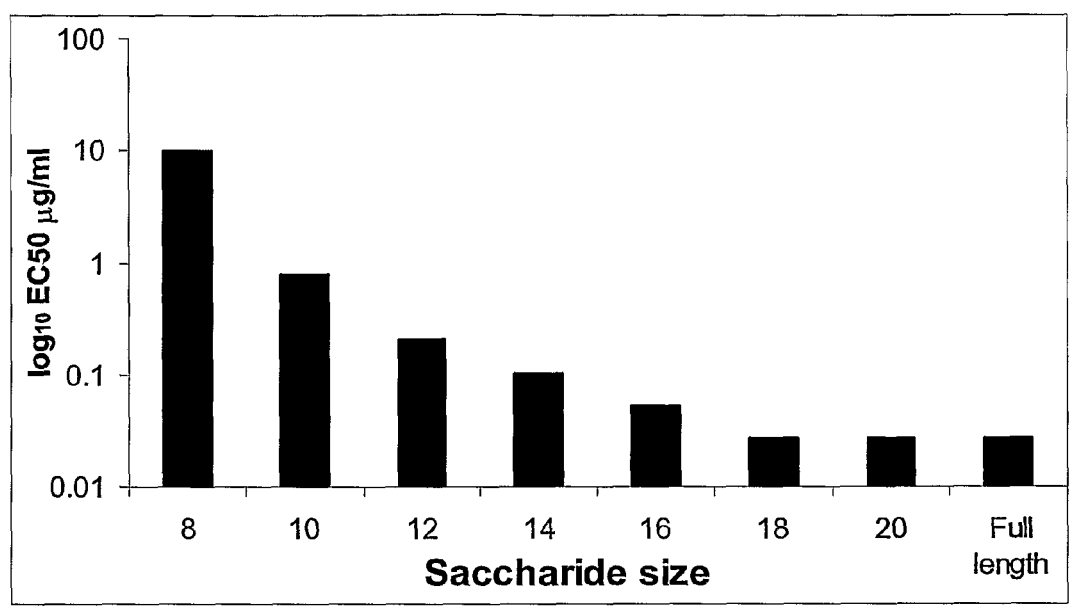

The present application is a national phase entry under 35 U.S.C. §371 of International Application No. PCT/GB2007/001895, filed May 23, 2007, published in English, which claims benefit of United Kingdom Patent Application No. 0610350.1, filed May 25, 2006. The disclosures of all of said applications are incorporated by reference herein.

The present invention relates to the prevention and/or treatment of neurodegenerative disorders.

The incidence of age-related diseases is growing as the life expectancy of the population increases. Alzheimer's disease (AD) is a fatal, progressive and irreversible disorder of the central nervous system whose symptoms include memory loss, confusion, impaired judgment, personality changes, disorientation and loss of language skills.

AD is characterized by cerebral deposition of neurofibrillary tangles and neurotoxic β-amyloid (Aβ). Cleavage of amyloid precursor protein (APP) by AD β-secretase (BACE-1, β-site amyloid precursor protein cleaving enzyme-1, β-secretase-1) is the first and rate-limiting step in generating the Aβ peptide, the main component of amyloid plaques. Cleavage of APP by α, β and γ secretases generates a variety of peptides, of which $A\beta_{1-40}$, $A\beta_{1-42}$, created by the sequential action of β and γ secretases, are amyloidogenic and neurotoxic. Increased susceptibility of APP to BACE-1 cleavage has been found in several pathological mutations of APP and so the regulation of BACE-1 activity has become a key pharmaceutical target.

Heparan sulphate (HS) has been identified as a constituent of amyloid plaques and its abilities to interact with amyloid proteins, peptides and fibrils, promote aggregation and enhance the stability of fibrils have been well documented. Soluble heparin and heparin analogues have also been shown to inhibit these processes both in vitro and in vivo.

Recently, a novel role for HS was revealed when its ability to directly regulate BACE-1 cleavage of APP was discovered. Bovine lung heparin (BLH), porcine mucosal HS and derivatives were found to inhibit BACE-1 activity, possibly by blocking access to the enzyme active site (Scholefield, Z. et al. *Journal of Cell Biology* 2003, 163, 97-107.), without interfering with APP processing by α or γ-secretases.

HS and its highly sulphated structural analogue heparin, are glycosaminoglycans consisting of 1,4 linked disaccharide repeat units of α-L-iduronic or β-D-glucuronic acid linked to either N-acetyl or N-sulfo-α-D-glucosamine. The principal positions of O-sulphation are C-2 of iduronate and C-6 of glucosamine as well as, more rarely, C-3 of glucosamine. Variable substitution during biosynthesis results in considerable sequence diversity.

Heparin, the widely used pharmaceutical that has a higher degree of sulphation and is more homogeneous than HS, acts as a potent anti-coagulant by increasing the rate of formation of irreversible complexes between antithrombin III and the serine protease clotting factors $X_a$ and IIa. Heparin has been extensively employed as an analogue of HS and is often a good activator of many biological processes involving HS. However, attenuation of the anticoagulant activity of heparin is vital if its derivatives are to be developed for use as novel pharmaceuticals.

Previous studies of the interaction of HS and other glycosaminoglycans with amyloidogenic pathways have concentrated on the direct interaction of heparin and other highly sulphated compounds with the amyloid proteins and peptides, rather than the enzymes that produce them. To date, however, relatively few studies concerning the structural requirements of HS activity in this respect have been undertaken.

In spite of BACE-1 activity being of fundamental importance to the generation of Aβ peptides and the development of AD, there are currently no effective therapies which target BACE-1. The use of unmodified heparin as a therapeutic agent against BACE-1 would doubtless lead to a number of side-effects, most notably an increased risk of internal bleeding and impaired blood clotting mechanisms. This is likely to preclude the clinical use of standard heparin saccharides since this would impose significant limits on the effective doses that could be used.

As the life expectancy of the population increases, the need for new effective therapies against age-related neurodegenerative disorders, such as AD, is becoming increasingly important.

An object of the present invention is to provide compounds for use in the prevention and/or treatment of neurodegenerative disorders.

According to a first aspect of the present invention there is provided a compound comprised of one or more disaccharide units, the or each disaccharide unit comprising a uronate moiety linked to a glucosamine moiety, wherein the 2-O atom of the uronate moiety is substantially substituted with a hydrogen atom, the 6-O atom of the glucosamine moiety is substantially substituted with a sulphate group and the 2-N atom of the glucosamine moiety is substituted with an atom or group other than a sulphate group for use in the prevention and/or treatment of a neurodegenerative disorder.

The present invention provides a compound which may be considered as an HS analogue that exhibits significantly reduced anticoagulant activities compared to HS while maintaining strong inhibitory activity against BACE-1.

It is preferred that at least around 60% of the 2-O atoms of the uronate moieties present in the compound are substituted with a hydrogen atom. More preferably around 75% or more of the uronate 2-O atoms are substituted with hydrogen atoms. It is still further preferred that higher levels (e.g. at least around 85-95%) of the uronate 2-O atoms carry hydrogen atoms. Most preferably all, i.e. 100%, of the 2-O atoms of the uronate moieties present in the compound are substituted with a hydrogen atom.

With regard to the 6-O atom of the or each glucosamine moiety present in the compound of the present invention, while any desirable level of sulphation may be used, provided the glucosamine 6-O atom(s) is/are substantially sulphated, it is preferred that the level of sulphation at least around 60%, more preferably at least around 75%. Conveniently at least around 85-95% of the glucosamine 6-O atoms are sulphated, and most preferably the 6-O atom of all glucosamine moieties are sulphated, equating to a 6-O glucosamine atom sulphation level of 100%.

Where the level of hydrogen substitution at the 2-O uronate atom and/or sulphate substitution at the 6-O glucosamine atom is less than 100%, it will be appreciated that compounds containing more than one disaccharide may comprise neighbouring disaccharides possessing a different pattern of 2-O uronate and/or 6-O glucosamine substitution.

For example, a compound according to the present invention may consist of four disaccharides and possess a level of hydrogen substitution at the 2-O uronate atom of 75%, such that three of the four disaccharides contain uronate moieties in which the 2-O atom carries a hydrogen atom. In this case, the three disaccharides containing hydrogen-substituted 2-O uronate atoms may be covalently linked to one another with the disaccharide containing the non-hydrogen-substituted 2-O uronate atom at one or other end of the hydrogen-substituted hexasaccharide. Alternatively, the disaccharide containing the non-hydrogen-substituted 2-O uronate atom may be provided in between any two of the three disaccharides containing the hydrogen-substituted 2-O uronate atoms.

By way of further example, an icosasaccharide compound according to the present invention possessing 60% 6-O glucosamine atom sulphation contains six disaccharides in which each glucosamine moiety is sulphated at the 6-O position. The six 6-O-sulphated disaccharides may be combined with the remaining four non-6-O-sulphated disaccharides (i.e. disaccharides not sulphated at the 6-O position of the glucosamine moiety) in any desirable linear arrangement, e.g. the 6-O-sulphated disaccharides may be linked together to form a 6-O-sulphated dodecasaccharide linked to a non-6-O-sulphated octasaccharide or, three of the 6-O-sulphated disaccharides may be linked together to provide a 6-O-sulphated hexaaccharide which is linked at one end first to a non-6-O-sulphated disaccharides followed by a repeating sequence of 6-O-sulphated and non-6-O-sulphated disaccharides.

The Scholefield study discussed above concluded that the most active BACE-1 inhibitor compound was N-acetylated heparin from bovine lung which is highly sulphated at both the 2-O and 6-O positions. (Scholefield, Z. et al. supra) Removal of the 2-O or 6-O sulphates decreased activity of the compound against BACE-1 substantially, suggesting that removal of one or more sulphates (other than the N-sulphate alone) would have a deleterious effect on the ability of the compound to inhibit BACE-1.

A further conclusion from this study was that BLH is a much better inhibitor of BACE-1 activity than HS. Given that heparin has approximately 2.6 to 2.9 sulphate groups per disaccharide whereas HS has approximately 1.5, the decreased activity of HS compared to heparin may be due, at least in part, to the reduction in charge associated with selective de-sulphation which might be expected to reduce protein binding. A link between degree of sulphation and the level of activity of heparin compared to HS has also been observed in another study in which HS proteoglycans having higher sulphation levels were observed to bind more strongly to fibroblast growth factors than HS proteoglycans with lower sulphation levels (Kreuger, J., P. Jemth, et al. *J Biochem* 2005, 389(Pt 1) 145-150.). A further factor which may have contributed to the result observed in the Scholefield study is that removal of the 2-O-sulphate group causes heparin to assume a different conformation of the iduronate ring and probably also the glycosidic linkage.

The work of Scholefield, Z. et al. and Kreuger, J. et al. therefore indicates that de-sulphation generally equates to lower activity. The compound forming the basis of the present invention is substantially de-sulphated at the 2-O position in the uronate moiety and completely de-sulphated at the 2-N position of the glucosamine moiety and would therefore be expected to exhibit significantly reduced activity compared to the corresponding compound containing 2-O and N-sulphate groups. Surprisingly however, the results of tests carried out in respect of the compound of the present invention (described in detail below) indicate that removal of both the 2-O and N-sulphates provides a compound with an unexpectedly high retention of BACE-1 inhibitory activity despite having had the overall sulphation level cut significantly.

A second aspect of the present invention provides use of a compound comprised of one or more disaccharide units, the or each disaccharide unit comprising a uronate moiety linked to a glucosamine moiety, wherein the 2-O atom of the uronate moiety is substantially substituted with a hydrogen atom, the 6-O atom of the glucosamine moiety is substantially substituted with a sulphate group and the 2-N atom of the glucosamine moiety is substituted with an atom or group other than a sulphate group in the preparation of a medicament for the prevention and/or treatment of a neurodegenerative disorder.

A third aspect of the present invention provides a method for preventing and/or treating a neurodegenerative disorder comprising administering to a subject a therapeutic amount of a compound comprised of one or more disaccharide units, the or each disaccharide unit comprising a uronate moiety linked to a glucosamine moiety, wherein the 2-O atom of the uronate moiety is substantially substituted with a hydrogen atom, the 6-O atom of the glucosamine moiety is substantially substituted with a sulphate group and the 2-N atom of the glucosamine moiety is substituted with an atom or group other than a sulphate group.

According to a fourth aspect of the present invention the compound employed in the various aspects of the present invention defined herein is produced from artificial source material(s) or naturally occurring source material(s).

The compound may be wholly or partially synthetic. The compound may be produced by chemical modification of a naturally occurring saccharide, such as porcine intestinal mucosal heparin (PIMH) or bovine lung heparin (BLH), which are HS analogues. PIMH is used in the Comparative Example described below.

Production of the compound according to the fourth aspect of the invention preferably comprises a depolymerisation process. The depolymerisation process is preferably selected from the group consisting of nitrous acid scission, bacterial lyase enzyme treatment, periodate oxidation, chemical beta-elimination under alkaline conditions, free radical treatment, and any combination thereof.

A fifth aspect of the present invention provides a method for the production of the compound forming part of the various aspects of the present invention defined herein, the method employing artificial source material(s) or naturally occurring source material(s).

The method preferably comprises a depolymerisation process. The depolymerisation process is preferably selected from the group consisting of nitrous acid scission, bacterial lyase enzyme treatment, periodate oxidation, chemical beta-elimination under alkaline conditions, free radical treatment, and any combination thereof.

The choice of depolymerisation process may, at least in part, affect the structure of one or more of the terminal groups of the compound as discussed in more detail below.

In the disaccharide repeating unit forming the basis of the compound employed in the present invention the uronate moiety, preferably derived from coupling a uronic acid residue to a glucosamine residue, may take any desirable epimeric form. The uronate moiety may be selected from the group consisting of an (α-L)iduronate moiety (as shown for convenience and by way of example only in Formulae (I), (II) and (III) below), a (β-D)glucuronate moiety and a (α-L) galacturonate moiety.

The substituents bonded to the 6-O uronate atom, 3-O uronate atom and the 3-O glucosamine atom are each separately selected from the group consisting of hydrogen, substituted or unsubstituted alkyl so as to form an O-ether sugar ring substituent, substituted or unsubstituted alkoxy, substituted or unsubstituted aryl, substituted or unsubstituted acyl so as to form an O-ester sugar ring substituent, substituted or unsubstituted amido (e.g. a phthalamido group), sulphate and phosphate. Moreover, the 6-C uronate carboxylate group may be modified to provide a 6-C uronate alcohol group or ester group.

The alkyl group bonded to any one of the 6-O or 3-O uronate atoms, 3-O glucosamine atom or ring carbon atoms may be linear or branched and is preferably a $C_{1-6}$ alkyl group, optionally substituted with one or more atoms or groups, such as halogen atoms (e.g. fluorine, chlorine or bromine) or aryl, acyl, amido (e.g. a phthalamido group) or phosphate groups.

The substituted or unsubstituted acyl group bonded to the 6-O or 3-O uronate atoms, 3-O glucosamine atom or ring carbon atoms may be linear (e.g. pentanoyl) or branched (e.g. pivaloyl) and is preferably a $C_{1-6}$ substituted or unsubstituted acyl group. The acyl group may be an arylacyl group, such as a benzoyl group. The acyl group may be substituted with one or more halogen atoms, particularly fluorine, chlorine or bromine atoms. Thus, preferred acyl groups are mono-, di- and tri-fluoroacetyl group. A further preferred acyl group is a phthaloyl group. Preferably the acyl group is selected from the group consisting of substituted or unsubstituted acetyl, substituted or unsubstituted propionyl and substituted or unsubstituted butanoyl. Most preferably the acyl group is an unsubstituted acetyl group.

The pattern of substitution in respect of the ring carbon atoms of the uronate and glucosamine moieties may be selected to confer desirable properties, such as degree of hydrophobicity, upon the disaccharide compound of the present invention. Each of the 2-, 3- or 6-carbon atoms of the uronate and/or glucosamine moiety may be substituted with a substituent selected from the group consisting of hydrogen, substituted or unsubstituted alkyl (preferably methyl or ethyl), substituted or unsubstituted alkoxy to form an ether group, substituted or unsubstituted aryl (e.g. benzyl), substituted or unsubstituted acyl (e.g acetyl), substituted or unsubstituted carboxyl to form an ester group, substituted or unsubstituted amido (e.g. a phthalamido group), sulphate and phosphate.

Compounds of the present invention may be obtained from polysaccharides by a number of appropriate depolymerisation processes. The terminal groups of compounds of the present invention may take any of a wide variety of forms depending upon the nature of the preparation method used. Moreover, compounds may comprise any number of monosaccharides, and the total number of monosaccharides in the compound may be odd or even.

The depolymerisation methods may include, as non-limiting examples, nitrous acid scission, bacterial lyase enzyme treatment, periodate oxidation, chemical beta-elimination under alkaline conditions or free radical treatment, either alone or in combination.

The non-reducing terminal monosaccharide may be a glucosamine residue or derivative thereof, or a uronate moiety (e.g. a (α-L)iduronate, (β-D)glucuronate or (α-L)galacturonate moiety) or derivative or fragment thereof, e.g. an (α-L) iduronate, (β-D)glucuronate or (α-L)galacturonate moiety incorporating a Δ4-5 unsaturated ring a C-to-C double bond between carbons 4 and 5 in the ring). Such unsaturation can arise, for example, when polysaccharide fragments forming the compound are made by digestion with a bacterial lyase enzyme or a chemical beta-elimination process (commonly used to fragment heparin/HS).

The reducing terminal monosaccharide may be a uronate moiety (e.g. a (α-L)iduronate, (β-D)glucuronate or (α-L) galacturonate moiety) or derivative thereof, a glucosamine moiety or derivative or fragment thereof, 2,5-anhydromannose, 2,5-anyhydro-mannitol, a 1,6 anhydro (bicyclic) ring structure, or a mannosamine residue. Production of the compound may involve nitrous acid digestion, in which case the reducing terminal monosaccharide is likely to be 2,5-anhydromannose, which is normally chemically reduced to a 2,5-anhydro-mannitol residue. Production of the compound using a chemical beta elimination process, in which case some reducing terminal residues can also be found as a 1,6 anhydro (bicyclic) structure, generally derived from 6-O-sulphated glucosamine residues. In addition, the chemical beta-elimination process can also cause epimerisation of glucosamine residues to form mannosamine residues.

In preferred embodiments of the above defined aspects of the present invention the compounds are represented by the Formula (I) below where it will be appreciated that the uronate moiety is represented by an (α-L)iduronate moiety for convenience only and that Formula (I) should be understood to encompass compounds in which the uronate moiety is (α-L)iduronate, (β-D)glucuronate or (α-L)galacturonate.

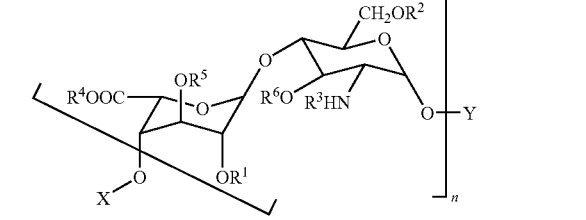

Formula (I)

In Formula (I) substantially all $R^1$ groups are hydrogen, substantially all $R^2$ groups are sulphate, $R^3$ is an atom or group other than sulphate, n is an integer equal to or greater than 1, $R^4$, $R^5$ and $R^6$ are each separately selected from the group consisting of hydrogen, substituted or unsubstituted alkyl, substituted or unsubstituted alkoxy, substituted or unsubstituted aryl, substituted or unsubstituted acyl, substituted or unsubstituted amido, sulphate and phosphate, and X and Y are each separately selected from the group consisting of hydrogen, a terminal monosaccharide group a terminal disaccharide group and/or fragments or derivatives thereof.

By way of example only, it will be appreciated that where the compound of the present invention consists solely of a saccharide unit of Formula (I) in which one of X and Y is hydrogen and the other one of X and Y is a terminal monosaccharide the compound as a whole will consist of an odd number of monosaccharide units, whereas, if X and Y are the same (i.e. X and Y are both hydrogen, monosaccharides or disaccharides) then the compound will consist of an even number of monosaccharide units. Moreover, if one of X and Y is a monosaccharide and the other of X and Y is a disaccharide then the compound will consist of an odd number of monosaccharides. Thus, Formula (I) and Formulae (II) and (III) that follow, are all intended to encompass compounds containing both odd and even numbers of monosaccharide units.

Where X is a terminal monosaccharide group it is preferred that X is a glucosamine moiety or derivative or fragment thereof. X may take the same structure as the glucosamine moiety in Formula (I) in which $R^2$, $R^3$ and $R^4$ are as defined above.

Where X is a terminal disaccharide group, X preferably has the structure of the bracketed disaccharide repeating unit such that the non-reducing terminal monosaccharide has the same general structure as the uronate moiety in Formula (I), i.e. an (α-L)iduronate, (β-D)glucuronate or (α-L)galacturonate moiety in which $R^1$, $R^4$ and $R^5$ are as defined above. Disaccharide unit X may include derivatives of one or both of the monosaccharides forming part of the bracketed disaccharide repeating unit. The non-reducing terminal monosaccharide may be an (α-L)iduronate, (β-D)glucuronate or (α-L)galacturonate moiety incorporating a Δ4-5 unsaturated ring (i.e. a C-to-C double bond between carbons 4 and 5 in the ring). Such unsaturation arises, for example, when polysaccharide fragments forming the compound are made by digestion with a bacterial lyase enzyme or a chemical beta-elimination process (commonly used to fragment heparin/HS).

Where Y is a terminal monosaccharide group, Y is preferably a uronate moiety or derivative or fragment thereof. Y preferably has the same general structure as the uronate moiety in Formula (I), i.e. an (α-L)iduronate, (β-D)glucuronate or (α-L)galacturonate moiety in which $R^1$, $R^4$ and $R^5$ are as defined above.

Where Y is a terminal disaccharide group, Y preferably has the same general structure to the bracketed disaccharide repeat of Formula (I) such that the reducing terminal monosaccharide, may have the same structure as the glucosamine moiety in Formula (I) in which $R^2$, $R^3$ and $R^4$ are as defined above. Disaccharide unit Y may include derivatives of one or both of the monosaccharides forming part of the bracketed disaccharide repeating unit. The reducing terminal monosaccharide may be 2,5-anhydro-mannitol, a 2,5-anhydromannose residue, a 1,6 anhydro (bicyclic) ring structure, or a mannosamine residue. Production of the compound may involve nitrous acid digestion, in which case the reducing terminal monosaccharide is likely to be 2,5-anhydro-mannitol, which is normally chemically reduced to a 2,5-anhydromannose residue. Production of the compound using a chemical beta elimination process, in which case some reducing terminal residues can also be found as a 1,6 anhydro (bicyclic) structure, generally derived from 6-O-sulphated glucosamine residues. In addition, the chemical beta-elimination process can also cause epimerisation of glucosamine residues to form mannosamine residues.

In preferred embodiments of the compound of Formula (I) $R^5$ and $R^6$ are both hydrogen, such that these preferred embodiments have the structure shown below in Formula (II) in which $R^1$, $R^2$, $R^3$, n, X and Y are as defined above in respect of Formula (I), and the uronate moiety is represented by an (α-L)iduronate moiety for convenience only and may be an (α-L)iduronate, (β-D)glucuronate or (α-L)galacturonate moiety.

Formula (II)

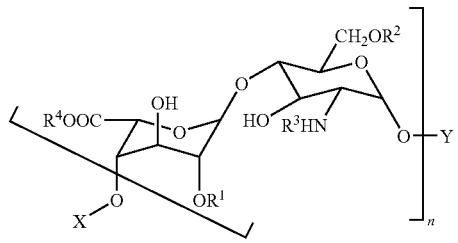

The 2-N atom of the glucosamine moiety ($R^3$ in Formulae (I) and (II) above) may be substituted with any desirable organic or inorganic chemical group subject to the proviso that the 2-N substituent group is not a sulphate ($SO_3^-$) group. The 2-N glucosamine atom is preferably substituted with a substituent selected from the group consisting of hydrogen, substituted or unsubstituted alkyl, substituted or unsubstituted aryl, substituted or unsubstituted acyl, substituted or unsubstituted amido, and phosphate.

The 2-N alkyl group may be linear, branched or cyclic and is preferably a $C_{1-6}$ alkyl group, optionally substituted with one or more atoms or groups, such as halogen atoms (e.g. fluorine, chlorine or bromine) or aryl, acyl, amido or phosphate groups.

The amido group bonded directly to the 2-N glucosamine atom and/or the amido group bonded to the alkyl group bonded to the 2-N glucosamine atom may take any convenient form, such as a methylamido, ethylamido or phthalamido group.

The substituted or unsubstituted acyl group bonded directly to the 2-N glucosamine atom and/or the acyl group bonded to the alkyl group bonded to the 2-N glucosamine atom may be linear (e.g. pentanoyl) or branched (e.g. pivaloyl) and is preferably a $C_{1-6}$ substituted or unsubstituted acyl group. The acyl group may be an arylacyl group, such as a benzoyl group. The acyl group may be substituted with one or more halogen atoms, particularly fluorine, chlorine or bromine atoms. Preferred N-acyl groups are mono-, di- and tri-fluoroacetyl group. A further preferred N-acyl group is a phthaloyl group. Preferably the 2-N glucosamine atom is substituted with an acyl group selected from the group consisting of substituted or unsubstituted acetyl, substituted or unsubstituted propionyl and substituted or unsubstituted butanoyl. Most preferably the glucosamine 2-N atom is substituted with an unsubstituted acetyl group, as in Formula (III) below.

With reference to the R groups and n defined above in Formula (I), in particularly preferred embodiments of the compound of the present invention all $R^1$ groups are hydrogen, all $R^2$ groups are sulphate, $R^3$ is an acetyl group, and $R^4$, $R^5$ and $R^6$ are all hydrogen. These preferred embodiments are represented by Formula (III) below where X and Y are as defined above in respect of Formula (I) and, as before, the uronate moiety may be an (α-L)iduronate (as shown for convenience only), (β-D)glucuronate or (α-L)galacturonate moiety.

Formula (III)

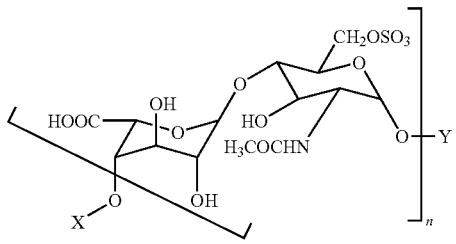

The compound employed in each aspect of the present invention may be of any appropriate length and may incorporate disaccharides of differing structure (i.e. possessing different substitution patterns) in any desirable linear sequence. Moreover, the compound of the present invention may be produced by suitable modification of a natural oligosaccharide or polysaccharide or a fragment thereof.

The compound of the present invention may consist of an odd or even number of monosaccharides. If the compound incorporates only disaccharide repeats then clearly the overall number of monosaccharide units in the compound will be an even number, however, it will be appreciated that the compound may include disaccharide repeats and a single terminal saccharide unit at one or other end of the molecule which would produce a compound consisting of an odd number of monosaccharides.

By way of example, with reference to Formula (I) above, the compound may be represented by one of the following three preferred structures (Formula (IV), (V) and (VI)) in which all R groups and n are as defined above in respect of Formula (I), and the uronate moiety is represented by an (α-L)iduronate moiety for convenience only and may be an (α-L)iduronate, (β-D)glucuronate or (α-L)galacturonate moiety.

In Formula (IV) X is a terminal glucosamine moiety of the same general structure as that included in the bracketed disaccharide repeating unit.

Formula (IV)

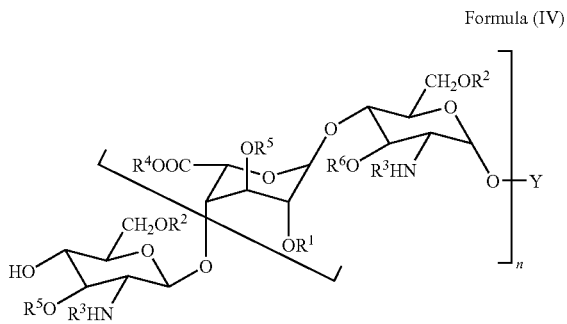

In Formula (V) Y is a terminal uronate moiety of the same general structure as that included in the bracketed disaccharide repeating unit.

Formula (V)

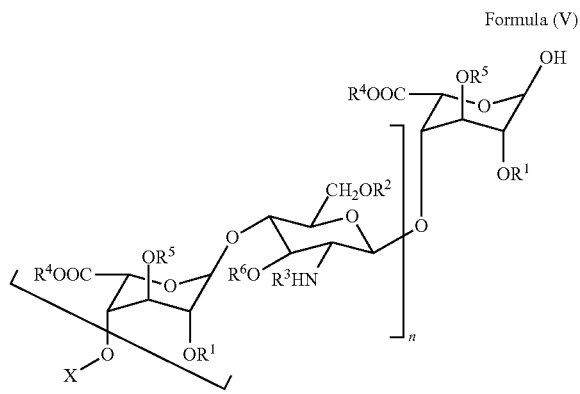

In Formula (VI) X is a terminal glucosamine moiety of the same general structure as that included in the bracketed disaccharide repeating unit and Y is a terminal uronate moiety of the same general structure as that included in the bracketed disaccharide repeating unit.

Formula (VI)

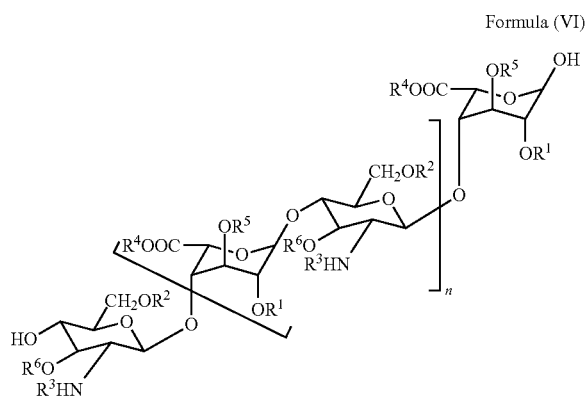

The Scholefield study concluded that oligosaccharides of 10 monosaccharides or more of BLH were required to inhibit activity of BACE-1 and no significant activity was observed in oligosaccharides below this size. (Scholefield, Z. et al. supra) Unexpectedly, it has been determined that compounds in accordance with the present invention containing fewer than 10 monosaccharides exhibit BACE-1 inhibitory activity. The compound according to each aspect of the present invention preferably comprises 4 to 24 monosaccharide units (e.g. preferably n=2 to 12, X=Y=H in Formulae (I) to (III) above). Compounds containing lower numbers of monosaccharides are preferred since it is envisaged that smaller compounds will more easily cross the blood brain barrier. More preferably the compound comprises 6 to 20 monosaccharide units (preferably n=3 to 10, X=Y=H, more preferably n=2 to 9, X=disaccharide, Y=H), yet more preferably 6 to 18 monosaccharide units (preferably n=3 to 9, X=Y=H, more preferably n=1 to 7, X=disaccharide, Y=disaccharide), and it is particularly preferred that the compound comprises 6 to 16 monosaccharide units (preferably n=3 to 8, X=Y=H, more preferably n=2 to 7, X=monosaccharide, Y=monosaccharide). Another preferred size range for the compound forming part of each aspect of the present invention is 6 to 16 monosaccharide units which equates to a preferred molecular weight range for the compound of approximately 1500 to 5000 Daltons.

While it is anticipated that the compound may find use in both human and veterinary medicine for the prevention and/or treatment of a number of neurodegenerative disorders, such as senile dementia, pre-senile dementia, multi-infarct dementia and other neurological disorders and lesions. The compound according to each aspect of the present invention is eminently suitable for use in the prevention and/or treatment of Alzheimer's disease.

It will be evident to the skilled person that the compound according to the first aspect of the present invention is eminently suitable for use in the preparation of a medicament for the prevention and/or treatment of a neurodegenerative disorder, particularly Alzheimer's disease, in accordance with the second aspect of the present invention.

The method for preventing and/or treating a neurodegenerative disorder forming the third aspect of the present invention preferably employs the compound according to the first aspect of the present invention.

A sixth aspect of the present invention provides a pharmaceutical composition for use in the prevention and/or treatment of a neurodegenerative disorder comprising a compound comprised of one or more disaccharide units, the or each disaccharide unit comprising a uronate moiety linked to a glucosamine moiety, wherein the 2-O atom of the uronate moiety is substantially substituted with a hydrogen atom, the 6-O atom of the glucosamine moiety is substantially substituted with a sulphate group and the 2-N atom of the glucosamine moiety is substituted with an atom or group other than a sulphate group.

The compound is preferably provided in the pharmaceutical composition forming the sixth aspect of the present invention in combination with a pharmaceutically acceptable carrier, diluent or excipient.

A seventh aspect of the present invention provides a compound comprised of one or more disaccharide units, the or each disaccharide unit comprising a uronate moiety linked to a glucosamine moiety, wherein the 2-O atom of the uronate moiety is substantially substituted with a hydrogen atom, the 6-O atom of the glucosamine moiety is substantially substituted with a sulphate group and the 2-N atom of the glucosamine moiety is substituted with an atom or group other than a sulphate group.

Employing the assay set out below in the Comparative Example the compound of the present invention preferably exhibits an $IC_{50}$ for BACE-1 inhibition of less than around 100 μg/ml, more preferably less than around 10 μg/ml, more preferably less than around 1 μg/ml, still more preferably less than around 0.1 μg/ml, and most preferably an $IC_{50}$ of less than approximately 0.05 μg/ml.

With regard to anti-coagulant activity, it is preferred that the compound of the present invention exhibits less than around 50% of the anti-coagulant activity of unmodified porcine intestinal mucosal heparin (PIMH). Preferably the inventive compound exhibits less than around 20%, more preferably less than around 5% of the anti-coagulant activity of unmodified PIMH. It is particularly preferred that the compound of the invention exhibits less than about 1%, still more preferably less than about 0.5% of the anti-coagulant activity of unmodified PIMH. It is further preferred that the compound according to the present invention exhibits anti-coagulant activity which is less than around 0.1%, and more preferably around 0.03% of the anti-coagulant activity of unmodified PIMH.

Preferably the therapeutic ratio of the inventive compound (calculated as the ratio of anti-BACE-1 activity (determined using the assay described below in the Comparative Example) to anti-serine protease clotting factor Xa activity) is greater than around 100, more preferably greater than around 500, more preferably around 1000 and most preferably greater than 1000. It is particularly preferred that the therapeutic ratio of the inventive compound is in the range 100 to 2000, more preferably 200 to 1500, and most preferably in the range 500 to 1500. In a particularly preferred embodiment of the present invention the compound of the present invention exhibits a therapeutic ratio of around 1092.

The compound of the invention may take a number of different forms depending, in particular on the manner in which the compound is to be used. Thus, for example, the compound may be provided in the form of a powder, tablet, capsule, liquid, ointment, cream, gel, hydrogel, aerosol, spray, micelle, transdermal patch, liposome or any other suitable form that may be administered to a person or animal. It will be appreciated that the vehicle of the compound of the invention should be one which is well tolerated by the subject to whom it is given and enables delivery of the compound to the brain.

The compound may be administered ocularly in the form of eye drops or eye ointments, or orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

The compound of the invention may be used in a number of ways. For instance, systemic administration may be required in which case the compound may, for example, be ingested orally in the form of a tablet, capsule or liquid. Alternatively the compound may be administered by injection into the blood stream. Injections may be intravenous (bolus or infusion) or subcutaneous (bolus or infusion). The compounds may be administered by inhalation (e.g. intranasally).

The compound may also be administered centrally by means of intracerebral, intracerebroventricular or intrathecal delivery.

The compound may also be incorporated within a slow or delayed release device. Such devices may, for example, be inserted on or under the skin and the compound may be released over weeks or even months. The devices may be particularly advantageous when a compound is used which would normally require frequent administration (e.g. at least daily ingestion of a tablet or daily injection).

It will be appreciated that the amount of a compound required is determined by biological activity and bioavailability which in turn depends on the mode of administration, the physicochemical properties of the compound employed and whether the compound is being used as a monotherapy or in a combined therapy. The frequency of administration will also be influenced by the above mentioned factors and particularly the half-life of the compound within the subject being treated.

Optimal dosages of the compound to be administered may be determined by those skilled in the art, and will vary with the particular compound in use, the strength of the preparation, the mode of administration, and the advancement of the disease condition. Additional factors depending on the particular subject being treated will result in a need to adjust dosages, including subject age, weight, gender, diet, and time of administration.

Known procedures, such as those conventionally employed by the pharmaceutical industry (e.g. in vivo experimentation, clinical trials, etc.), may be used to establish specific formulations of compounds and compositions and precise therapeutic regimes (such as daily doses of the compounds and the frequency of administration).

Generally, a daily dose of between 0.01 μg/kg of body weight and 1.0 g/kg of body weight of the inventive compound may be used for the treatment of AD depending upon which specific compound is used. More preferably, the daily dose is between 0.01 mg/kg of body weight and 100 mg/kg of body weight.

Daily doses may be given as a single administration (e.g. a daily tablet for oral consumption or as a single daily injection). Alternatively, the compound used may require administration twice or more times during a day. As an example, patients with AD may be administered as two or more daily doses of between 25 mgs and 5000 mgs in tablet form. A patient receiving treatment may take a first dose upon waking and then a second dose in the evening (if on a two dose regime) or at 3 or 4 hourly intervals thereafter. Alternatively, a slow release device may be used to provide optimal doses to a patient without the need to administer repeated doses.

This invention provides a pharmaceutical composition comprising a therapeutically effective amount of the compound of the invention and, preferably, a pharmaceutically acceptable vehicle. In the subject invention a "therapeutically effective amount" is any amount of a compound or composition which, when administered to a subject suffering from a disease against which the compounds are effective, causes reduction, remission, or regression of the disease. A "subject" is a vertebrate, mammal, domestic animal or human being. In the practice of this invention the "pharmaceutically acceptable vehicle" is any physiological vehicle known to those of ordinary skill in the art useful in formulating pharmaceutical compositions.

In one embodiment, the amount of the compound in the composition according to the sixth aspect of the present invention is an amount from about 0.01 mg to about 800 mg. In another embodiment, the amount of the compound is an amount from about 0.01 mg to about 500 mg. In another embodiment, the amount of the compound is an amount from about 0.01 mg to about 250 mg. In another embodiment, the amount of the compound is an amount from about 0.1 mg to about 60 mg. In another embodiment, the amount of the compound is an amount from about 1 mg to about 20 mg.

In one embodiment, the pharmaceutical vehicle employed in the composition forming the fourth aspect of the present invention may be a liquid and the pharmaceutical composition would be in the form of a solution. In another embodiment, the pharmaceutically acceptable vehicle is a solid and the composition is in the form of a powder or tablet. In a further embodiment, the pharmaceutical vehicle is a gel and the composition is in the form of a suppository or cream. In a further embodiment the compound or composition may be formulated as a part of a pharmaceutically acceptable transdermal patch.

A solid vehicle employed in the composition according to the sixth aspect of the present invention can include one or more substances which may also act as flavoring agents, lubricants, solubilizers, suspending agents, fillers, glidants, compression aids, binders or tablet-disintegrating agents; it can also be an encapsulating material. In powders, the vehicle is a finely divided solid which is in admixture with the finely divided active ingredient. In tablets, the active ingredient is mixed with a vehicle having the necessary compression properties in suitable proportions and compacted in the shape and size desired. The powders and tablets preferably contain up to 99% of the active ingredient. Suitable solid vehicles include, for example, calcium phosphate, magnesium stearate, talc, sugars, lactose, dextrin, starch, gelatin, cellulose, polyvinylpyrrolidine, low melting waxes and ion exchange resins.

Liquid vehicles may be used in preparing solutions, suspensions, emulsions, syrups, elixirs and pressurized compositions according to the sixth aspect of the present invention. The compound of the first aspect of the present invention can be dissolved or suspended in a pharmaceutically acceptable liquid vehicle such as water, an organic solvent, a mixture of both or pharmaceutically acceptable oils or fats. The liquid vehicle can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid vehicles for oral and parenteral administration of the compound forming the first aspect of the present invention include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the vehicle can also be an oily ester such as ethyl oleate and isopropyl myristate. Sterile liquid vehicles are useful in sterile liquid form compositions for parenteral administration. The liquid vehicle for pressurized compositions can be halogenated hydrocarbon or other pharmaceutically acceptable propellent.

The compound forming the first aspect of the present invention can be administered orally in the form of a sterile solution or suspension containing other solutes or suspending agents (for example, enough saline or glucose to make the solution isotonic), bile salts, acacia, gelatin, sorbitan monoleate, polysorbate 80 (oleate esters sorbitol and its anhydrides copolymerized with ethylene oxide) and the like.

Liquid pharmaceutical compositions which are sterile solutions or suspensions can be utilized by for example, intramuscular, intrathecal, epidural, intraperitoneal or subcutaneous injection. Sterile solutions can also be administered intravenously. The inventive compounds may be prepared as a sterile solid composition according to the sixth aspect of the present invention which may be dissolved or suspended at the time of administration using sterile water, saline, or other appropriate sterile injectable medium. Vehicles are intended to include necessary and inert binders, suspending agents, lubricants, flavorants, sweeteners, preservatives, dyes, and coatings.

The compound forming part of the present invention is eminently suitable for use in prophylactic treatment. By the term "prophylactic treatment" we include any treatment applied to prevent, or mitigate the effect of a neurological disorder, such as AD. The prophylactic treatment may be given, for example, periodically to a person who is of a predetermined minimum age or who is genetically predisposed to a neurological disorder. Alternatively the prophylactic treatment may be given on an ad hoc basis to a person who is to be subjected to conditions which might make the onset of a neurological disorder more likely.

This invention will be better understood from the examples that follow. However, one skilled in the art will readily appreciate that the specific methods and results discussed are merely illustrative of the invention as described more fully in the claims which follow thereafter.

Figure 2:
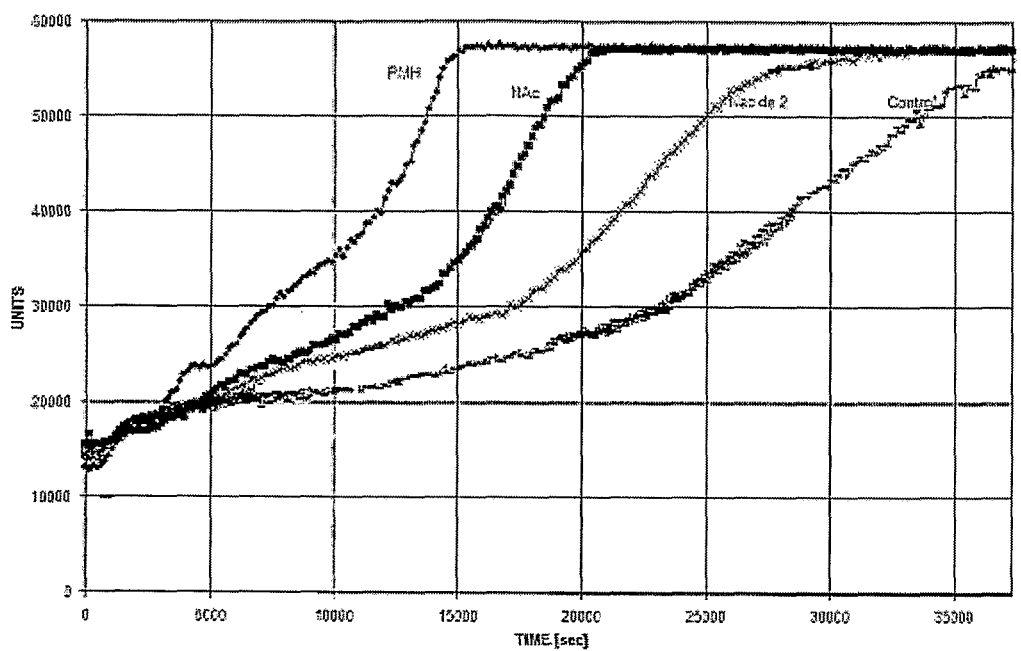

An embodiment of the present invention will now be described by way of example only with reference to the following non-limiting Comparative Example, in which:

FIG. 1 is a plot of the activity of unmodified PIMH fragments on BACE-1 inhibition as a function of saccharide size as referred to in Example 1; and FIG. 2 is a plot of the effect of modified heparin derivatives on the rate of aggregation of A-β peptide as referred to in Example 2. The rate of aggregation that occurs in the absence of any added compound is shown as "control".

EXAMPLE 1: COMPARATIVE EXAMPLE

The availability and pharmaceutical use of BLH have declined recently following concerns over the transmissible spongiform encephalopathies (TSEs) prompting the inventors to examine BACE-1 inhibition activity with porcine intestinal mucosal heparin (PIMH), which possesses higher levels of β-glucuronic acid, compared to BLH but is both widely available and poses no known TSE risk.

A modified panel of PIMH derivatives (Formula (VII); listed in Table 1) were prepared by the methods set out in the Appendix. Patterns of O-, N-sulphation and N-acetylation were varied over the predominant disaccharide repeating structure permitting a systematic study of activity. The panel was evaluated for ability to inhibit BACE-1 cleavage of APP, potency as anti-coagulants (anti-factor Xa), and for their ability to inhibit other aspartyl protease family members.

One of the PIMH derivatives, compound 4 (Formula (VIII) below, which corresponds to Formula (III) where the uronate moiety is an (α-L)iduronate moiety) is a preferred embodiment of the compound of the present invention.

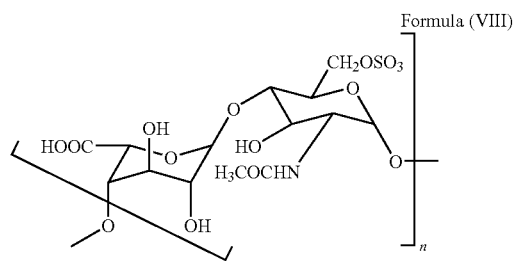

Formula (VIII)

The results of the tests carried out are shown in Table 1 and discussed in more detail below.

TABLE 1

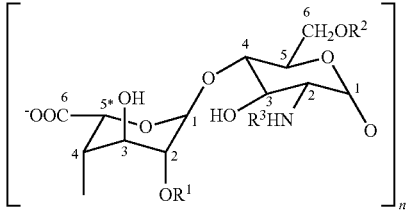

Formula (VII)

| Compound | | $R_1$ | $R_2$ | $R_3$ | $IC_{50}$ (μg/ml) | $R^2$ of $IC_{50}$ | Anti-coagulant activity | Therapeutic ratio (BACE/Xa) |
|---|---|---|---|---|---|---|---|---|
| 1 | PIMH | $SO_{3-}$ | $SO_{3-}$ | $SO_{3-}$ | 0.028 | 0.998 | 100% | 1 |
| 2 | N-acetyl | $SO_{3-}$ | $SO_{3-}$ | $COCH_3$ | 0.031 | 0.995 | 0.03% | 3136 |
| 3 | UA-2-OH | H | $SO_{3-}$ | $SO_{3-}$ | 0.053 | 0.995 | 0.4% | 147 |
| 4 | UA-2-OH, N-Acetyl | H | $SO_{3-}$ | $COCH_3$ | 0.091 | 0.999 | 0.03% | 1092 |
| 5 | GlcN-6-OH | $SO_{3-}$ | H | $SO_{3-}$ | 0.100 | 0.996 | 0.5% | 61 |
| 6 | GlcN-6-OH, N-acetyl | $SO_{3-}$ | H | $COCH_3$ | 0.410 | 0.995 | 0.03% | 237 |
| 7 | UA-2-OH, GlcN-6-OH | H | H | $SO_{3-}$ | 0.786 | 0.994 | 0.03% | 123 |
| 8 | UA-2-OH, GlcN-6-OH, N-acetyl | H | H | $COCH_3$ | >100 | n/a | 0.03% | 1 |
| 9 | Per-sulphated # | $SO_{3-}$ | $SO_{3-}$ | $SO_{3-}$ | 0.053 | 0.998 | 35.0% | 2 |
| 10 | 3-amino-1-propanesulfonic acid | — | — | — | No activity | n/a | n/a | n/a |

*In Formula (VII) the configuration shown at $C_5$ is α-L-iduronic acid.

In Table 1 anticoagulant activities are expressed as a percentage of PIMH (defined as 100%). Substitution pattern is defined by $R^1$, $R^2$ and $R^3$, corresponding to position-2 of iduronate, -6 of glucosamine and -2 of glucosamine respectively. The therapeutic ratio was calculated from the $IC_{50}$ against BACE-1/anticoagulant activity. UA—Uronic acid, either α-L-iduronic or β-D-glucuronic acid; GlcN—α-D-glucosamine. # compound (9) was sulphated at position-3 in both the iduronate and glucosamine residues. The $IC_{50}$ values are, of course, dependent upon the nature of the assay used.

BACE-1 Inhibitory Activity

The BACE-1 inhibitory properties of BLH with substitution patterns corresponding to (1), (2), (3) and (5) have been tested previously by Scholefield et al. using BLH as the starting material. (Scholefield, Z. et al. supra)

In vitro cleavage of APP by BACE-1 was measured using a FRET peptide cleavage assay. Following unmodified PIMH (1), the most effective inhibitor of BACE-1 was de-N-sulphated, re-N-acetylated PIMH (2). Ranked third and fourth most active, with similar $IC_{50}$ values, were 2-O de-sulphated (3) and the inventive compound (4) 2-O de-sulphated/N-acetylated PIMH which has a pattern of substitution which was not previously reported. This indicates that neither the N- or 2-O sulphates are absolute requirements for high level activity when accompanied by 6-O sulphation. Preferred inventive compound (4) was therefore the most active mono. sulphated compound.

Removal of the 6-O-sulphate resulted in the least active di-sulphated compound (compound (5)). Compound (4) was more active than either 6-O-desulphated (5) or 6-O-desulphated/N-acetylated heparin (6). This was an unexpected result in view of the fact that compound (4) has a lower number of sulphate groups per disaccharide than compound (5) and the same number of sulphate groups per disaccharide to compound (6).

The least active mono-sulphated compound was compound (7) in which both the 2-O- and 6-O-sulphates had been removed leaving only the N-sulphate group. Removal of all sulphate groups to provide compound (8) almost abolished the anti-BACE-1 activity of PIMH.

The activities of the inventive compound (4) and compound (5) which has a pattern of substitution previously reported in relation to BLH (Scholefield, Z. et al. supra) indicated a significant role for the 6-O-sulphate in the inhibition of BACE-1.

The inventors also examined the effect of per-sulphated heparin (compound (9)), which was sulphated additionally at position-3 in both the iduronate and glucosamine residues. This compound unexpectedly exhibited a similar $IC_{50}$ to unmodified PIMH. The lack of a direct correlation between sulphation level and BACE-1 inhibitory activity demonstrated clearly that activity was not simply related to charge density.

While the inventors do not wish to be bound by a particular theory it is likely that the relationship between activity and substitution pattern is a complex one, which may depends on conformational effects, because both iduronate ring and glycosidic linkage geometries depend subtly on substitution pattern.

The inventors also examined the effect of 3-amino-1-propanesulfonic acid (3APS, Alzehemed™) (compound 10), a compound described as a "heparin mimetic", which is undergoing clinical trials for the treatment of AD and whose proposed mechanism of action is inhibition of Aβ aggregation. 3APS did not inhibit BACE-1, even at high concentrations (1000 μg/ml), indicating that its "heparin mimetic" activities do not extend to inhibition of BACE-1.

Anticoagulant Activity

Removal of the N-sulphate and replacement with an N-acetyl group had the greatest effect on reducing the ability of the chemically modified PIMH to interfere with the antithrombin III/factor Xa complex. The anti factor Xa activities of compounds possessing N-acetyl groups, including preferred inventive compound (4), were at least 3000-fold lower than PIMH (Table 1).

Removal of either the 2-O or 6-O sulphate groups, on the other hand, reduced the antithrombin III/factor Xa activity by approximately 200-fold.

It is well-established that the anti-factor Xa activity of heparin/HS is due to the specific pentasaccharide sequence —4) GlcNAc(6S) α(1-4) GlcA β(1-4) GlcNS(3,6S) α(1-4) IdoA(2S) α(1-4) GlcNS(6S) α(1—.

The presence of a 3-O-sulphate group within the central glucosamine residue is vital for anti-factor Xa activity and its removal results in its virtual abolition, while removal of either the N-sulphate from the central glucosamine or 2-O-sulphate from the iduronate residue, have less dramatic, but nonetheless, deleterious effects.

The removal of N-sulphate groups and their replacement with N-acetyl in heparin derivatives (modification of compound (1) to (2)) explains the loss of anticoagulant activity exhibited by compound (2), but de-O sulphation in iduronate, which occurs under highly basic conditions, also resulted in a substantial reduction in anti-factor Xa activity and has two potential causes. The first is the removal of the 2-O-sulphate group (as in preferred inventive compound (4)) but a second modification also occurs in rare glucosamine residues bearing both 3-O sulphate and N-sulphate (e.g. in the pentasaccharide sequence AGA*IA), involving the formation of an N-sulphated aziridine group with loss of the 3-O-sulphate.

Other de-O-sulphated heparin derivatives such as compound (5) or (8), prepared under different conditions, do not contain this modification and the reduction in their activities can only be attributed to the loss of the relevant groups within the pentasaccharide sequence. In particular, it is noteworthy that the 3-O-sulphate group is stable under mild de 6-O-sulphation conditions.

Inhibition of Other Proteases Structurally Related to BACE-1

The closest structural relatives to BACE-1 are the aspartyl proteases pepsin, cathepsin D and renin. These enzymes have functions in digestion, regulation of blood pressure and lysosomal degradation of proteins respectively. An effective inhibitor of BACE-1 could potentially also interact with these, causing unwanted side effects if administered pharmaceutically.

Activity against the aspartyl proteases of compounds (1), (2) and (3), which have patterns of substitution investigated previously in the Scholefield study, and preferred inventive compound (4), was measured in FRET peptide cleavage assays. None of the compounds exerted an inhibitory effect on renin, even at concentrations up to 1000 μg/ml.

Interestingly, unmodified PIMH (compound (1)) showed some inhibitory activity against both pepsin and cathepsin D, with $IC_{50}$ values of 0.23 μg/ml and 0.1 μg/ml respectively. N-acetyl (compound 2) and preferred compound (4) N-acetyl/Ido-2-OH PIMH showed a marked decrease in inhibitory activity against both pepsin and renin, when compared to PIMH (compound 1).

The $IC_{50}$ for N-acetyl PIMH (compound 2) against pepsin was 3.27 μg/ml, which is 14 fold less potent than PIMH (compound 1); whereas N-acetyl/Ido-2-OH PIMH (preferred compound 4) did not inhibit pepsin at >1000 μg/ml.

The $IC_{50}$ values for compounds (2) and (3) against cathepsin D were 0.27 μg/ml and 0.77 μg/ml respectively. Thus, the modified forms of PIMH exhibiting high levels of anti-BACE-1 activity, including preferred compound (4), do not significantly inhibit renin, pepsin or cathepsin D and have much higher $IC_{50}$ values than unmodified PIMH.

Inhibition of BACE-1 by Oligosaccharides

Full length PIMH was enzymatically digested, fractionated by gel-filtration chromatography and the fragments used to determine the effective size for inhibition of BACE-1 in the FRET peptide cleavage assay.

FIG. 1 is a plot of the activity of unmodified PIMH fragments on BACE-1 inhibition as a function of saccharide size.

A first feature to note from FIG. 1 is that activity was observed in respect of octasaccharides indicating a minimum requirement for high anti-BACE-1 activity of around 8 saccharides. The fact that the results shown in FIG. 1 indicate a lower minimum length for activity than the value of 10 saccharides suggested by previous work (Scholefield, Z. et al. supra) suggests that activity would be expected at saccharide levels as low as 2. Activity at lower levels compared to the results of the Scholefield study is unexpected given that there is evidence that polysaccharides and oligosaccharides do not possess the same level of activity so it can not be expected that a smaller fragment of a polysaccharide will act in the same manner as the full length molecule. A shift in inhibitory activity (ten-fold increase) was observed with deca- compared to octasaccharides suggesting a more preferred minimum length of 10 saccharides.

At 18 saccharide units the activity was equivalent to full length PIMH. These data are promising regarding in vivo administration because heparin saccharides as large as 3,000 Da (equivalent to ~12 saccharides) can cross the blood-brain barrier (BBB).

Another possible side-effect of standard heparin administration is heparin-induced thrombocytopenia (HIT) caused by the production of antibodies to heparin-platelet factor 4 complexes, but reduction in molecular weight and sulphation level has been shown to ameliorate this.

The retention of anti-BACE-1 activity in oligosaccharides with reduced levels of sulphation, such as preferred inventive compound (4), shows significant promise for pharmaceutical use by improving the potential uptake into the brain and through the reduction of anticoagulation and other unwanted side-effects. N-acetyl PIMH (compound 2) and N-acetyl/Ido-2-OH PIMH (preferred compound (4)) exhibited high BACE-1 inhibitory activity with very little anticoagulant activity.

Preferred compound (4) therefore represents an excellent candidate for use in the prevention and/or treatment of neurodegenerative disorders, such as AD.

APPENDIX TO EXAMPLE 1

Preparation of Modified Heparins

Chemically modified heparin compounds (1) to (9) were prepared by the following combinations of reactions (a) to (g) below:

(1). PIMH starting material (Celsus Labs, Cincinnati, Ohio);
(2). N-acetyl heparin (d) (f);
(3). Ido 2-de-O-sulphated heparin (a);
(4). Ido 2-de-O-sulphated, N-acetylated heparin (a) (d) (f);
(5). 6-O-desulphated heparin (b) (e);
(6). 6-O-desulphated, N-acetylated heparin (b) (f);
(7). 6-O-desulphated, 2-O-desulphated heparin (c) (e);
(8). 6-O-desulphated, 2-O-desulphated, N-acetylated heparin (c) (f); and
(9). Per-sulphated heparin (g) (e).

Compounds were characterized by $^1$H and $^{13}$C NMR as previously described. (Yates, E. A.; Santini, F.; Guerrini, M.; Naggi, A.; Torri, G. et al. *Carbohydrate Research* 1996, 294, 15-27.) Compounds were desalted, lyophilized and re-suspended in the appropriate buffer prior to assay.

Chemical Reactions (a) Selective removal of iduronate 2-O-sulphate was achieved as described by Jaseja and Perlin. (Jaseja, M.; Rej, R. N.; Sauriol, F.; Perlin, A. S. *Can. J. Chem.* 1989, 67, 1449-1456.) Note that there is concomitant modification in the small number of N- and 3-O-sulphated glucosamine units.

(Santini, F.; Bisio, A.; Guerrini, M.; Yates, E. A. *Carbohydrate Research* 1997, 302, 103-108.)

(b) Selective removal of glucosamine 6-O-sulphate was carried out according to a modification (Yates, E. A. et al. supra.) of the method described. (Inoue, S.; Miyawaki, M. *Analytical Biochemistry* 1975, 65, 164-174.)

(c) Complete removal of O- and N-sulphates was achieved using solvolytic de-sulphation by the method described. (Inoue, S.; Miyawaki, M. supra.)

(d) Selective de-N-sulphation was carried out employing controlled solvolytic de-sulphation under kinetic control as described. (Inoue, Y.; Nagasawa, K. *Carbohydrate Research* 1976, 46, 87-95.)

(e) Re N-sulphation was achieved by use of trimethylamine-.sulfur trioxide complex as described. (Lloyd, A. G.; Embery, G.; Fowler, L. J. *Biochemical Pharmacology* 1971, 20, 637-648.)

(f) Re N-acetylation employed acetic anhydride in saturated sodium bicarbonate. (Yates, E. A. et al. supra.)

(g) Complete O-sulphation of all available hydroxyl groups was carried out using excess sulfur trioxide pyridine complex on the tetrabutylammonium salt of heparin in pyridine as described (Yates, E. A.; Santini, F.; De Cristofano, B.; Payre, N.; Cosentino, C. et al. *Carbohydrate Research* 2000, 329, 239-247.) followed by re-N-sulphation (Lloyd, A. G. et al. supra.) taking precautions to avoid formation of an unusual N-sulfoaziridine modification. (Yates, E. A.; Santini, F.; Bisio, A.; Cosentino, C. *Carbohydrate Research* 1997, 298, 335-340.)

NMR Spectroscopy

The effectiveness of chemical treatments was monitored by $^1$H and $^{13}$C NMR at 500 MHz and 125 MHz respectively ($D_2O$, 27° C.). Chemical shifts; $\delta$/ppm (external standard) were in full agreement with well-defined model compounds. (Yates, E. A. et al. supra.)

Preparation of Sized Oligosaccharides

Porcine mucosal heparin and chemically modified N-acetyl heparin were digested with 100 mU heparatinase II (Ibex Technologies Inc., Montreal, Canada), per 100 mg in 100 mM sodium acetate, 0.1 mM calcium acetate, pH 7.0. The digested fragments were separated by gel filtration chromatography (Superdex-30, Amersham Pharmacia, UK, 2000 mm×30 mm, 100 mM ammonium bicarbonate) and identified by reference to size-defined authentic standards.

Determination Of BACE-1 Inhibition By In Vitro Peptide Cleavage Assay

The ability of the compounds to inhibit BACE-1 cleavage of APP was assessed using a fluorescent resonance energy transfer (FRET) peptide cleavage assay employing the FRET peptide 5-FAM-Glu-Val-Asn-Leu-Asp-Ala-Phe-Lys(QXL520)-OH, containing the Swedish amino acid variant (Anaspec, Inc., CA, USA). When intact, the amino terminal fluorophore is quenched, but upon enzymatic cleavage the fluorophore is released from quencher and fluoresces (520 nm). Assays were performed in triplicate in 96 well black plates (20 mM sodium acetate, 0.1% Triton-X-100, pH 4.5; 2.5 µM peptide per well and $4.0 \times 10^{-3}$ units/well of recombinant human BACE-1 (Sigma)). The appropriate controls for enzyme activity and background fluorescence were employed and plates were incubated (1 h, 25° C., stopped with 2.5 M sodium acetate) Inhibitors were added in a concentration range from 1000-0.0001 µg/ml. Fluorescence 480ex/520em was measured on a Polarstar plate reader (BMG LabTechnologies, UK) and data were analysed by plotting $\log_{10}$ concentration of inhibitor against percent inhibition and fitting a four parameter sigmoidal curve using BioDataFit 1.02 (Chang Bioscience, USA).

Anticoagulant Activity

Anti Factor Xa activity was measured against a porcine mucosal heparin (PIMH) standard of known activity (Sigma, UK) using a diagnostic grade Coatest Heparin test kit (Chromogenix, MA, USA), adapted to a 96 well plate format, reading $A_{405}$ (Polarstar plate reader (BMG LabTechnologies, UK)).

Activity Against Other Proteases

The ability of compounds to inhibit the structurally related proteases pepsin and cathepsin D (Sigma, UK) was measured by FRET cleavage assay (5 pmol enzyme/well, EnzChek Protease Assay kit (Molecular Probes, UK) according to manufacturer's instructions). Activity against human recombinant renin (Cayman Chemical, MI, USA), was measured by FRET peptide cleavage assay (0.08 pMoles enzyme/well, using the Renin Substrate 1 (Molecular Probes, Invitrogen, UK) according to manufacturer's instructions. $IC_{50}$ values were calculated as described above.

EXAMPLE 2

The inventors conducted further experiments to illustrate the efficacy of compounds according to the first aspect of the invention for treating neurodegenerative conditions.

Unless stated otherwise, the methodology out lined in Example 1 (and the appendix thereof) was employed in this work.

N-modified Heparins with 2-O-Desulphation as BACE Inhibitors

A number of examples of N-modified heparins with 2-O-desulphation were tested as BACE inhibitors in comparison to parental (unmodified) heparin. These polysaccharides are modified by de-N-sulphation to create glucosamine residues, followed by substitution of a variety of alternative chemical groups at the free amino groups and appropriate desulphation at the 2-O position.

N-modified heparins which are modified by 2-O-desulphation are potent BACE inhibitors with reduced off-target activities. By way of example, N-acetyl-de-2-O-sulphated PMH (6-O-sulphate content of approximately 82%, 2-O-sulphate content of <0.1%) has an $EC_{50}$ approximately 3-fold lower than unmodified PMH (Table 2). A further example is N-propionyl-de-2-O-sulphated PMH (6-O-sulphate content of approximately 82%, 2-O-sulphate content of <0.1%), which has an $EC_{50}$ approximately 8-fold lower than unmodified PMH, but an anti-factor Xa activity around $1/100^{th}$ that of intact heparin, highlighting the unpredictable sensitivity of these derivatives to changes in structure, in this case, N-substitution. In addition, all of the above N-modified heparins displayed very weak anticoagulant activity (between $1/100$ and $1/3000^{th}$ that of unmodified PMH).

TABLE 2

| Compound | $EC_{50}$ (µg/ml) | Anticoagulant activity (%) |
|---|---|---|
| Standard heparin | 0.027 | 100 |
| N-acetyl de-2-OS heparin[1] | 0.089 | <0.03 |
| N-propionyl de-2OS heparin[2] | 0.210 | ~1 |

[1]The 6-O-sulphate content approx. 82%, 2-O-sulphate content <0.1%.
[2]The 6-O-sulphate content approx. 82%, 2-O-sulphate content <0.1%.

Effects of Modified Heparins on Amyloid-β Peptide Aggregation

In addition to anticoagulant activity, a further possible side effect of heparin directly relevant to treating neurodegenerative disorders is their known ability to enhance aggregation of the amyloid-β (Aβ) peptide (Watson, D. J., Lander, A. D. and Selkoe, D. J. (1997) Heparin-binding properties of the amyloidogenic peptides Aβ and amylin. Dependence on aggregation state and inhibition by Congo red. *J Biol Chem*, 272, 31617-24). Reduction of this activity would be a desirable property. The inventors therefore investigated the activity of modified heparins compared to parental porcine mucosal heparin in assays of Aβ aggregation. The results of the investigation are presented in FIG. 2.

The maximum enhancement is observed with intact heparin "PMH". It was observed that de-sulfation of heparin caused marked reductions in this activity. Several compounds (for example, N-acetylated heparin "NAc" and ido-2-desulfated, N-acetylated heparin "Nac de 2") possess desirable BACE-1 inhibitory activity and favourable anti-coagulant activities (anti-factor Xa)(Patey et al (2006) 49 6129-6132) also possess improved rates (i.e. 50 and 100% slower respectively) of A-β aggregation. Specifically, at a concentration of 100 μg/ml, either N-acetylated or 2-de-O-sulphated PMH resulted in a 50% increase in the time taken to reach half-maximal peptide aggregation, and N-acetylated, 2-de-O-sulphated PMH produced a 100% increase to near control levels (i.e. the aggregation rate observed with no added heparin). Thus, preferred chemical modifications in accordance with the present invention as defined in claim 1 significantly reduce the ability of heparin to promote Aβ aggregation, and consequently possess improved therapeutic ratios in this regard compared to unmodified heparin.

Aβ aggregation assay protocol

The Aβ peptide was prepared by addition of 1 ml of hexafluoro-2-propanol to 1 mg Aβ peptide (Amyloid β Protein Fragment 1-42; Sigma A9810) and disaggregation at room temperature for 1 hour. The resulting material was divided into 50 μl (50 μg) aliquots and dried in Speed Vac for approximately 2 hours, followed by storage at −20° C. The Thioflavin T (Sigma T-3516) solution was prepared as a 5 mM solution in 50 mM Glycine-NaOH pH 8.5, and stored in the dark at 4° C. Thioflavin T assay buffer comprising 20 μl Thioflavin T solution with 50 μl 1M DTT and 430 μl assay Buffer (10 mM HEPES/100 mM NaCl pH 7.4) was kept on ice. 50 μl of 20 mM NaOH was added to 50 μg of Aβ peptide. 2.5 ml of Thioflavin T assay buffer was then added to this Aβ peptide solution, making "Aβ buffer". The remaining 2.5 ml of Thioflavin T assay buffer was the blank buffer, and both were kept on ice. Six replicates of sample dilutions (1:1 in assay buffer) were pipetted into a 96 well black plate (Greiner 655076; 100 μl/well) and the plate was kept on ice. 100 μl/well of Aβ buffer was added to the samples (in triplicate), and 100 μl/well of the blank buffer added to a further three sample replicates. The 96 well plate was read (450 nm excitation wavelength and 490 nm emission wavelength), taking a reading every 150 seconds for 250 cycles one plate reader set at 37° C.

The invention claimed is:

1. A compound for use in the treatment of Alzheimer's disease, wherein the compound has the formula (I)

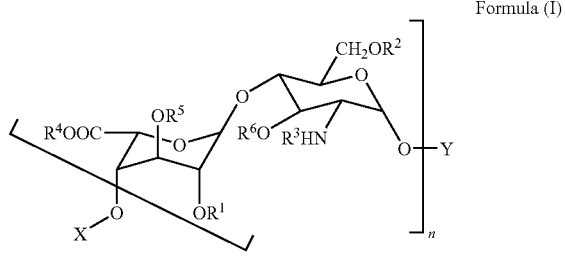

Formula (I)

wherein at least 60% of the $R^1$ groups are hydrogen, at least 60% of the $R^2$ groups are sulphate, $R^3$ is selected from the group consisting of substituted or unsubstituted alkyl, substituted or unsubstituted aryl, substituted or unsubstituted acyl, substituted or unsubstituted amido and phosphate; n is an integer which is 2 to 12, and $R^4$, $R^5$ and $R^6$ are each separately selected from the group consisting of hydrogen, substituted or unsubstituted alkyl, substituted or unsubstituted alkoxy, substituted or unsubstituted aryl, substituted or unsubstituted acyl, substituted or unsubstituted amido, sulphate and phosphate, and X and Y are each separately selected from the group consisting of hydrogen, a terminal monosaccharide group, and a terminal disaccharide group, wherein for each and every "n", each $R^3$, $R^4$, $R^5$, and $R^6$ is the same.

2. A compound according to claim 1, wherein the substituted or unsubstituted acyl group is a $C_{1-6}$ substituted or unsubstituted acyl group.

3. A compound according to claim 1, wherein the substituted or unsubstituted acyl group is selected from the group consisting of substituted or unsubstituted acetyl, substituted or unsubstituted propionyl and substituted or unsubstituted butanoyl.

4. A compound according to claim 1, wherein $R^5$ and $R^6$ are hydrogen.

5. A compound according to claim 1, wherein $R^4$ is hydrogen.

6. A compound for use in the treatment of Alzheimer's disease, wherein the compound has the formula (III)

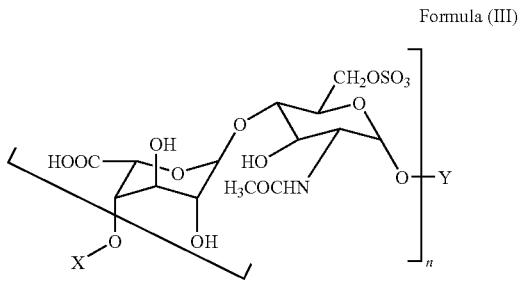

Formula (III)

wherein n is an integer which is 2 to 12, and X and Y are each separately selected from the group consisting of hydrogen, a terminal monosaccharide group and a terminal disaccharide group.

7. A compound according to claim 6, wherein n is 3 to 8.

8. A method for treating Alzheimer's disease comprising administering to a subject a therapeutic amount of a compound according to claim 1 or claim 6.

9. A pharmaceutical composition for use in the treatment of Alzheimer's disease comprising a compound according to claim 1 or claim 6.

10. A method for the production of a compound according to claim 1 wherein the method comprises a) subjecting a heparin derivative to one or more processes selected from the group consisting of de-sulphation, re-sulphation and addition of the $R^3$ group; and b) subjecting the heparin derivative or the reacted heparin derivative of a) to a depolymerisation process selected from the group consisting of nitrous acid scission, bacterial lyase enzyme treatment, periodate oxidation, chemical beta-elimination under alkaline conditions, free radical treatment, and any combination thereof.

* * * * *